(12) United States Patent
Zimbron

(10) Patent No.: US 11,320,378 B2
(45) Date of Patent: May 3, 2022

(54) METHODS, SYSTEMS, AND DEVICES FOR MEASURING IN SITU SATURATIONS OF PETROLEUM AND NAPL IN SOILS

(71) Applicant: E-Flux, LLC, Fort Collins, CO (US)

(72) Inventor: Julio Zimbron, Fort Collins, CO (US)

(73) Assignee: E-Flux, LLC, Fort Collins, CO (US)

( * ) Notice: Subject to any disclaimer, the term of this patent is extended or adjusted under 35 U.S.C. 154(b) by 0 days.

(21) Appl. No.: 16/896,472

(22) Filed: Jun. 9, 2020

(65) Prior Publication Data
US 2020/0300761 A1 Sep. 24, 2020

Related U.S. Application Data

(63) Continuation of application No. 16/047,491, filed on Jul. 27, 2018, now Pat. No. 10,677,729.

(60) Provisional application No. 62/537,682, filed on Jul. 27, 2017.

(51) Int. Cl.
| | |
|---|---|
| *G01T 1/20* | (2006.01) |
| *G01N 21/64* | (2006.01) |
| *G01N 33/24* | (2006.01) |
| *E21B 49/00* | (2006.01) |
| *G01N 21/85* | (2006.01) |
| *G01N 33/18* | (2006.01) |

(52) U.S. Cl.
CPC ........... *G01N 21/645* (2013.01); *E21B 49/00* (2013.01); *G01N 21/64* (2013.01); *G01N 21/6456* (2013.01); *G01N 21/8507* (2013.01); *G01N 33/18* (2013.01); *G01N 33/24* (2013.01); *G01N 33/241* (2013.01); *G01N 2021/6417* (2013.01); *G01N 2021/6482* (2013.01); *G01N 2021/6497* (2013.01); *G01N 2021/855* (2013.01)

(58) Field of Classification Search
CPC .. G01N 21/645; G01N 33/18; G01N 21/6456; G01N 33/241; G01N 21/64; G01N 21/8507; G01N 33/24; G01N 2021/6497; G01N 2021/855; G01N 2021/6482; G01N 2021/6417; E21B 49/00
See application file for complete search history.

(56) References Cited

U.S. PATENT DOCUMENTS

| | | | |
|---|---|---|---|
| 5,316,950 A | * | 5/1994 | Apitz .................. G01N 21/274 422/82.07 |
| 5,548,115 A | | 8/1996 | Ballard et al. |
| 5,604,582 A | | 2/1997 | Rhoads et al. |

(Continued)

FOREIGN PATENT DOCUMENTS

| | | | | |
|---|---|---|---|---|
| CA | 2935841 C | * | 7/2018 | ............. G01J 3/433 |
| JP | 2004239793 A | | 8/2004 | |

(Continued)

*Primary Examiner* — Kiho Kim
(74) *Attorney, Agent, or Firm* — Dentons Davis Brown, P.C.; Matthew Warner-Blankenship

(57) ABSTRACT

Improved devices, systems and methods for measuring in situ saturations of non-aqueous phase liquids and/or petroleum in media such as soil. A clear or otherwise UV-transparent well for detecting fluorescence in a soil column having a transparent casing and an oil sensing device positioned in the well configured to monitor the soil column. A method for real-time estimation of LNAPL saturations in media, including emplacing a UV-transparent well in the media and recording fluorescence in the media via an oil sensing device.

19 Claims, 7 Drawing Sheets

(56) References Cited

U.S. PATENT DOCUMENTS

| | | |
|---|---|---|
| 9,952,156 B2 | 4/2018 | Boss et al. |
| 2006/0199270 A1 | 9/2006 | Pamas et al. |
| 2007/0046289 A1 | 3/2007 | Troxler |
| 2007/0187617 A1 | 8/2007 | Kong et al. |
| 2009/0208072 A1 | 8/2009 | Seibel et al. |
| 2010/0068821 A1 | 3/2010 | St. Germain |
| 2013/0027540 A1 | 1/2013 | Ito |
| 2013/0132001 A1 | 5/2013 | Yacout et al. |
| 2015/0076335 A1 | 3/2015 | Vasilyev et al. |
| 2016/0084815 A1 | 3/2016 | Cuero Rengifo et al. |
| 2016/0290102 A1 | 10/2016 | Pelletier et al. |
| 2017/0003224 A1* | 1/2017 | Boss ................. G01N 21/6486 |
| 2017/0059488 A1 | 3/2017 | Wolf et al. |

FOREIGN PATENT DOCUMENTS

| | | | |
|---|---|---|---|
| WO | 9323741 | 11/1993 | |
| WO | WO-2015050550 A1 * | 4/2015 | ........... E21B 21/066 |

* cited by examiner

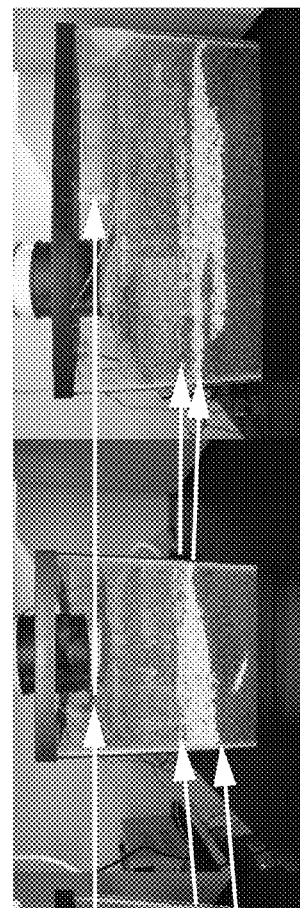
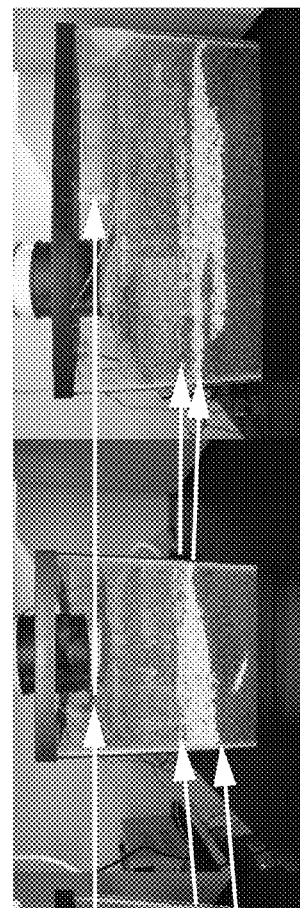

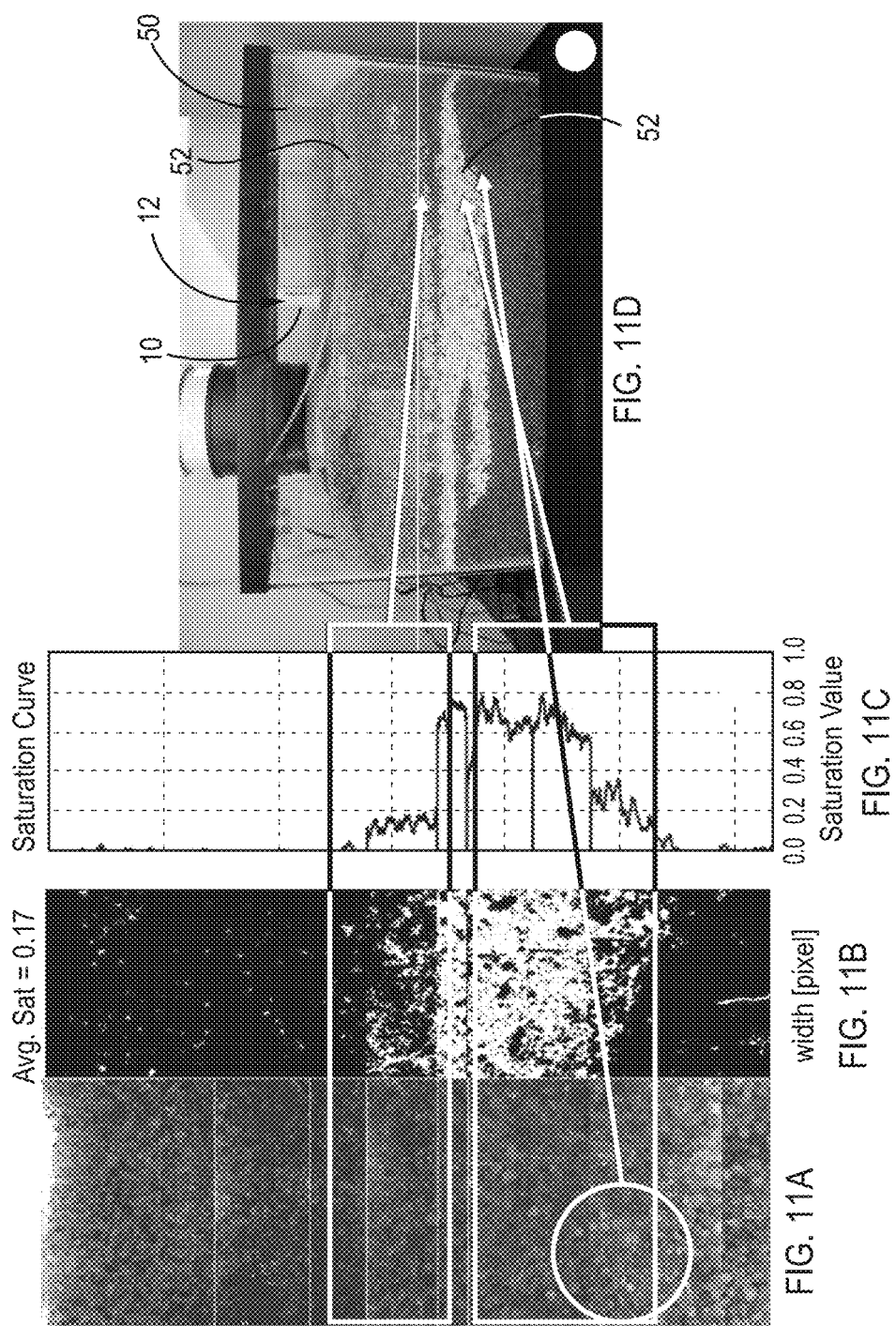

METHODS, SYSTEMS, AND DEVICES FOR MEASURING IN SITU SATURATIONS OF PETROLEUM AND NAPL IN SOILS

CROSS-REFERENCE TO RELATED APPLICATION(S)

This application is a continuation of U.S. application Ser. No. 16/047,491, filed Jul. 27, 2018, entitled "Method, Systems, and Devices for Measuring In Situ Saturations of Petroleum and NAPL in Soils," which claims priority to U.S. Provisional Application No. 62/537,682 filed Jul. 27, 2017, each of which are hereby incorporated by reference in their entirety.

TECHNICAL FIELD

The disclosed technology relates generally to improved devices, systems and methods for measuring in situ saturations of non-aqueous phase liquids and/or petroleum in media such as soil.

BACKGROUND OF THE INVENTION

In situ monitoring of petroleum in soils is done using two commonly used techniques. One is direct sensing of petroleum thickness in wells with an oil-water interface probe (OWIP). In this method, a sensor attached to a tape measure is lowered into the petroleum-containing well. The sensor indicates (typically by emitting a beeping sound) when it reaches the air-petroleum and the petroleum-water interfaces.

Another in situ petroleum monitoring technique is a one-time survey using laser induced fluorescence (LIF). This technique uses a LIF sensor mounted to a drill probe. The LIF probe shines a UV laser and detects the fluorescence response of the petroleum hydrocarbon in the soil the probe penetrates. This technique was developed by the US Army Core of Engineers and was patented in the early-mid 1990s. The technique is currently commercialized by Dakota Technologies, Inc. (DTI) and the LIF one-time survey equipment are available therefrom. At least two other commercial enterprises hold licenses from DTI: Matrix and Columbia Technologies.

The disadvantage of the OWIP method is that the well itself acts as the largest pore in the ground, and tends to accumulate much more petroleum than the geologic formation, thus resulting in an inaccurate measurement. FIG. 1 shows the results of a sand tank experiment in which a simulated well (against the sand tank glass window) show both the petroleum thickness in the well and the petroleum in the formation. In this experiment, the petroleum is diesel with a small concentration of fluorescent dye tracer. There is a large difference between the petroleum well thickness (what the OWIP method would sense) and the actual distribution in the formation. The petroleum in the well does not reflect the immobile LNAPL below the water table (surrounded by water), nor the residual saturations in the vadose zone (the mostly air-filled part of the soil column above the water table). Additional effects such as heterogeneities in the soil can exacerbate these differences. For example, petroleum confined between fine lenses of fine pore materials, such as clay, can show up in wells even though there is none in the formation at the water table.

LIF is an widely used method tested by the EPA's Technology Verification Program. The limitation of LIF is that it requires drilling with every measuring event. The implications are that it is a destructive method (each bore hole can only be used once) and that it requires large equipment and personnel mobilization efforts associated with every event of drilling and sampling. It can be coupled with other high resolution measurements, with the associated devices attached to the drilling equipment point (such as, for example, a hydraulic profiling tool or membrane interface probe). FIG. 2 shows a schematic diagram of the equipment used (http://www.columbiatechnologies.com/services/#HRVP)

There is a need in the art for an improved method, system, and device for measuring in situ saturations of petroleum and non-aqueous phase liquid (NAPL) in soils.

BRIEF SUMMARY

Discussed herein are various devices, systems, and methods relating to measuring in situ saturations of non-aqueous phase liquids and/or petroleum in media such as soil.

In one Example, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a UV-transparent well for detecting fluorescence in a soil column, including a casing including a transparent window; and an oil sensing device positioned in the well configured to monitor the soil column. Other embodiments of this aspect include corresponding computer systems, apparatus, and computer programs recorded on one or more computer storage devices, each configured to perform the actions of the methods.

Implementations may include one or more of the following features. The well further including a UV light source. The well further including an oil sensing device. The well where the oil sensing device is a fluorescence sensing device. The well where the oil sensing device is a UV camera. The well where the oil sensing device is a fiber optic device in operable communication with a spectrometer. The well where the oil sensing device is a laser-induced fluorescence device. Implementations of the described techniques may include hardware, a method or process, or computer software on a computer-accessible medium.

One Example aspect includes a UV-transparent well for detecting fluorescence in a soil column, including: a UV-transparent well, a UV light source; and a fluorescence sensing device. Other embodiments of this aspect include corresponding computer systems, apparatus, and computer programs recorded on one or more computer storage devices, each configured to perform the actions of the methods.

Implementations may include one or more of the following features. The well further including a fiber optic optical device configured to transmit and receive UV light to and from the source to the soil column. The well further including a computer configured to perform a binarization algorithm. The well where the computer is configured to evaluate in situ soil saturations. Implementations of the described techniques may include hardware, a method or process, or computer software on a computer-accessible medium.

One Example includes a method for real-time estimation of LNAPL saturations in media, including: emplacing a UV-transparent well in the media; and recording fluorescence in the media via an oil sensing device. Other embodiments of this aspect include corresponding computer systems, apparatus, and computer programs recorded on one or more computer storage devices, each configured to perform the actions of the methods.

Implementations may include one or more of the following features. The method where the UV-transparent well is emplaced in a soil column. The method further including generating fluorescence in at least one formation associated to contaminants by exposing the media to a UV light. The method where the recording florescence includes capturing images of the fluorescence using a miniature digital camera and/or a spectrometer. The method further including processing captured digital images of the fluorescence to establish the location of contaminant. The method further including quantifying soil pore contamination saturation via digital imaging binarization. Implementations of the described techniques may include hardware, a method or process, or computer software on a computer-accessible medium.

While multiple embodiments are disclosed, still other embodiments of the disclosure will become apparent to those skilled in the art from the following detailed description, which shows and describes illustrative embodiments of the disclosed apparatus, systems, and methods. As will be realized, the disclosed apparatus, systems, and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows hydraulic profiling tool results (relative permeability).

FIG. 5B shows the blue LIF signal (relative fluorescence, blue signal).

FIG. 5C shows the red LIF signal (relative fluorescence, red signal).

FIG. 5D shows the green LIF signal (relative fluorescence, green signal).

FIG. 5E shows temperature (° C.).

FIG. 6A is an original digital image adjusted to binarize it (white pixels indicate fluorescence and NAPL presence, while black ones reflect the lack of it).

FIG. 6B is a binary picture processed by averaging values across each elevation (values of 1 for white, 0 for black).

FIG. 6C is a chart depicted average NAPL saturations at each elevation.

FIG. 9A depicts a side views of a simulated well. The simulated contaminant appears as bright yellow, and only does so when excited by UV light.

FIG. 9B depicts an endlong view of a simulated well. The simulated contaminant appears bright yellow, and only does so when excited by UV light.

FIG. 9C depicts a side view of a simulated well. The simulated contaminant appears as bright yellow, and only does so when excited by UV light.

FIG. 10A shows the saturated contaminant (LNAPL) thickness of the image of FIG. 9A.

FIG. 10B shows the saturated contaminant (LNAPL) thickness of the image of FIG. 9B.

FIG. 10C shows the saturated contaminant (LNAPL) thickness of the image of FIG. 9C.

FIG. 11A is a close-up photograph within UV transparent well of FIG. 9.

FIG. 11B is a binarized rendering of FIG. 11A, showing contamination in white.

FIG. 11C is a saturation average for the binarized rendering of FIG. 11B.

FIG. 11D depicts the example simulated well used in FIGS. 11A-11C.

DETAILED DESCRIPTION

The various embodiments disclosed or contemplated herein relate to methods, systems, and devices for detecting fluorescence of petroleum in soils though a UV transparent material, instead of traditional well materials such as PVC pipe (typically slotted or screened at discrete intervals or entirely).

In accordance with certain implementations, the device for detecting fluorescence of petroleum is a UV-transparent well casing that enables direct detection and measurement of LNAPL through the well in a non-destructive manner. The various embodiments include the well casing being used in combination with an oil sensing device positioned therein.

Figure 3:
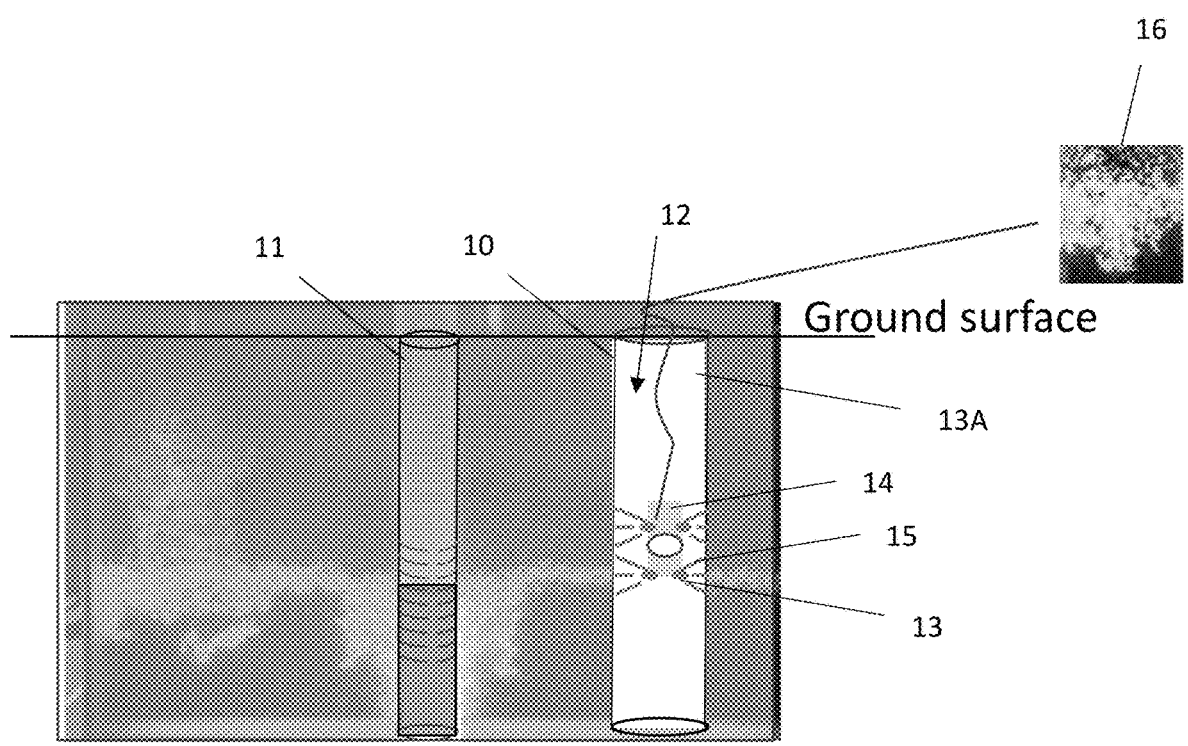
FIG. 3 is an Illustration of use of the disclosed in situ well, according to one embodiment (right) next to a traditional monitoring well (left).

FIG. 3 depicts one embodiment of a UV-transparent well casing 10 forming a dry well 12. A traditional well 11 is also depicted. In this embodiment, the well 12 is dry because the casing 10 is not slotted and is sealed or "plugged" at the bottom so that external fluids do not drain into the well 12. In this configuration, the UV-transparent well casing 10 can be used as a transparent window into the ground by which an oil sensing device 14 positioned in the well 12 can monitor any point in the soil column (above and below the water saturation level).

In this embodiment, a combination of ambient natural light 13A and a UV light source 13 disposed within the well 12 illuminate the UV-transparent well casing 10. A sensing device 14 (in this case a digital camera) is disposed within the well 12 so as to detect the fluorescence 15 of the petroleum or NAPL. The sensing device 14 is in operational communication with a computer or other display device (not shown) and is thereby able to generate an image 16 of the fluorescence 15, which is shown schematically in FIG. 3. It is understood that such an image 16 is displayed on the computer or display device 17). It is further understood that the use of natural light in combination with the UV light enables the visualization of additional soil features such as grain size, colors, and the like.

An additional advantage of the sealed well casing 10 is that the distribution of fluids in the soil adjacent to the casing 10 will not be influenced by the well itself (as would be the case in a typical well installation). The sealed well casing 10 ensures that the well 12 is not hydraulically connected to the formation, thereby avoiding the high bias caused by the well acting as both the largest pore in the formation and as a point of zero pressure (hydraulically connected to the ambient air). Thus, the sealed casing 10 results in LNAPL saturations more representative of the formation when the saturations are sensed through the casing 10 by fluorescence methods.

In one alternative, the well casing 10 is not sealed or plugged.

Figure 4:
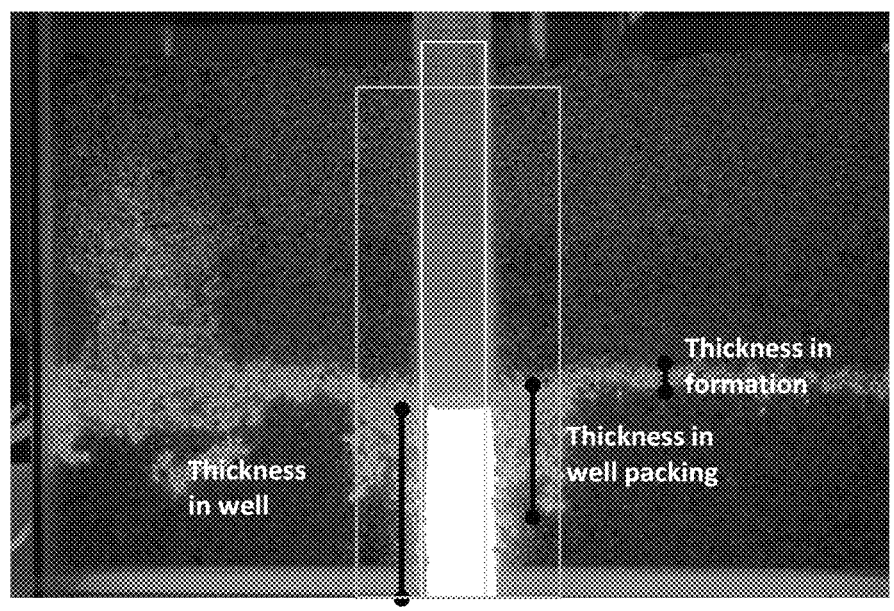
FIG. 4 is a cutaway side view depicting how well construction affects measurement next to well boring.

In one embodiment, the method of placing the well casing 10 includes not adding any external materials to fill in any portions of the hole remaining from the drilling of the well. As shown in FIG. 4, a typical well is constructed by drilling a hole, and while the hollow drilling stem is in the ground, a well casing is positioned in the hole. The void around the well casing created by the hole can be filled in using one of two different standard techniques: (1) adding external materials (typically coarse sand), or (2) allowing the native formation to collapse while the drilling stem is removed.

The addition of external materials, which is depicted in FIG. 4, would cause inaccurate measurements using the methods, systems, and devices disclosed herein. That is, the accuracy of the fluorescence measurements is dependent on monitoring soils as similar to the natural formation as possible, and the use of external materials would significantly alter the natural formation. Thus, certain embodiments of the method disclosed herein include allowing the native formation to collapse while the drilling stem is removed.

According to another embodiment, the method can also include freezing the ground in place prior to drilling (to minimize soil and petroleum disturbance). CSU is currently working on such a technology. That is, CSU is pursuing in situ soil characterization by nuclear magnetic resonance ("NMR") in combination with freeze drilling to preserve the part of the formation below groundwater while drilling.

Returning to FIG. 3, the sensing device 14 can be a device that senses the presence of petroleum upon excitation by UV light source 13 and photography (upon exposure to UV light), spectrometry (such as a fiber optic device, such as a cable, connected to a spectrometer), or laser-induced fluorescence (such as a LIF probe). Alternatively, any known oil sensing technology, such as, for example, any optically-based oil sensing technology, can be utilized.

The various UV transparent materials that can be used in the various well casing implementations herein include clear PVC, polymethyl pentene ("PMP"), UV transparent acrylic, and glass. In certain embodiments, the clear PVC or the UV transparent acrylic can be special or unique formulations. In one specific example, the UV transparent acrylic is commercially available from Ridout Plastics.

As mentioned above, certain devices and methods disclosed and contemplated herein utilize fluorescence to determine the amount of petroleum in the solid. Fluorescence consists of excitation with UV light (non-visible), which generates emission of light (typically in the visible range) in the fluorescing compounds. Fluorescing compounds typically have a chemical structure with alternating double bonds (including aromatics). Petroleum hydrocarbon fluoresces, and the response varies with the specific petroleum composition. It is understood that in various implementations, the response can be characterized by the quantity and characteristics of light emitted, such as by measuring red, green and blue ("RGB") emissions and their relative abundance.

According to another embodiment, a camera utilizing visible light photography can be positioned in the well casing 10 to perform a qualitative assessment of the geologic formation. This can be done qualitatively to determine the order of magnitude of the soil type (based on particle size) or more quantitatively by standard methods (to determine particle size distribution based on digital imaging). Although it is customary for geologists to record detailed boring logs (including particle size at discrete intervals) after core collection (either in the field or in the lab), such records can be lost or might be inconsistent. The use of the well casing embodiments disclosed or contemplated herein enables reviewing this information at any time in a non-destructive way.

Figures 5A, 5B, 5C, 5D, 5E:
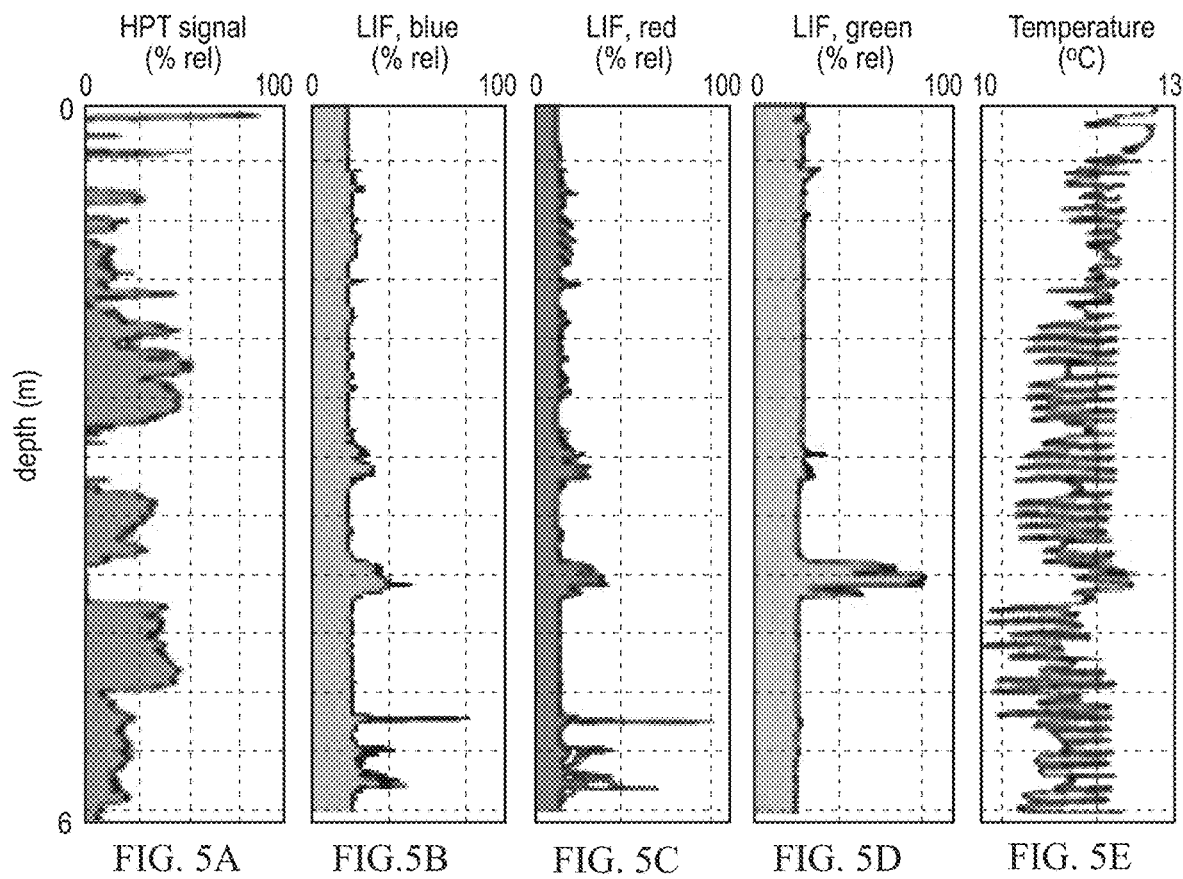
FIGS. 5A-E are an example LIF report from Columbia Technologies, where LIF intensity is shown as a function of depth in soil.

As mentioned above, according to one embodiment, the oil sensing device 14 positioned in the well casing 10 can be a LIF probe (which includes the UV light source 13). LIF uses a pulsed UV laser to induce fluorescence. Typically the fluorescence signal is separated in three channels (one for each primary color). Hydrocarbons produce a characteristic fluorescence pattern (combination of primary colors), based on hydrocarbon composition. FIG. 5 shows the results of a LIF profile in contaminated soil. This example can be found online at www.columbiatechnologies.com/membrane-interface-probe.

Figure 1:
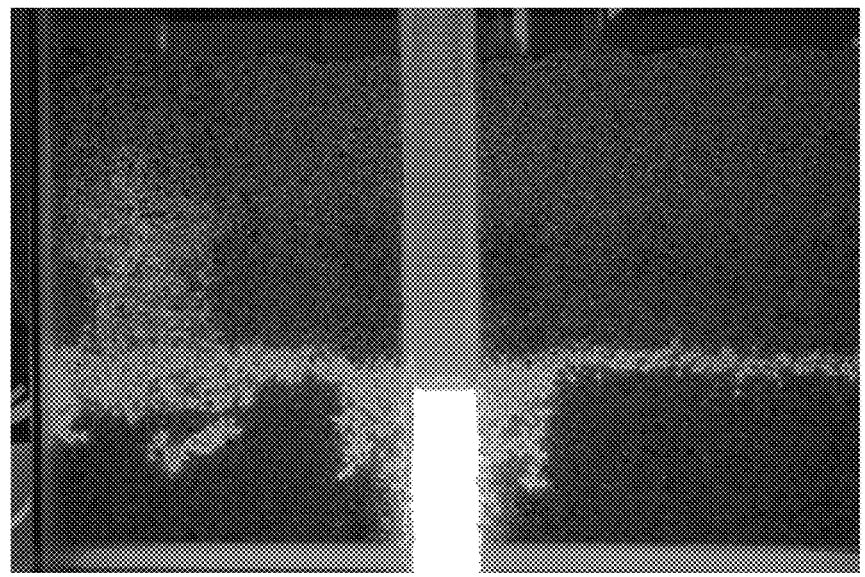
FIG. 1 is a cutaway side view of a petroleum visualization experiment in a sand tank (with a glass window) showing petroleum distribution in the well and the formation. Petroleum hydrocarbon (diesel) is dyed with a fluorescent dye and shows with a bright yellow color under UV light.
Figure 2:
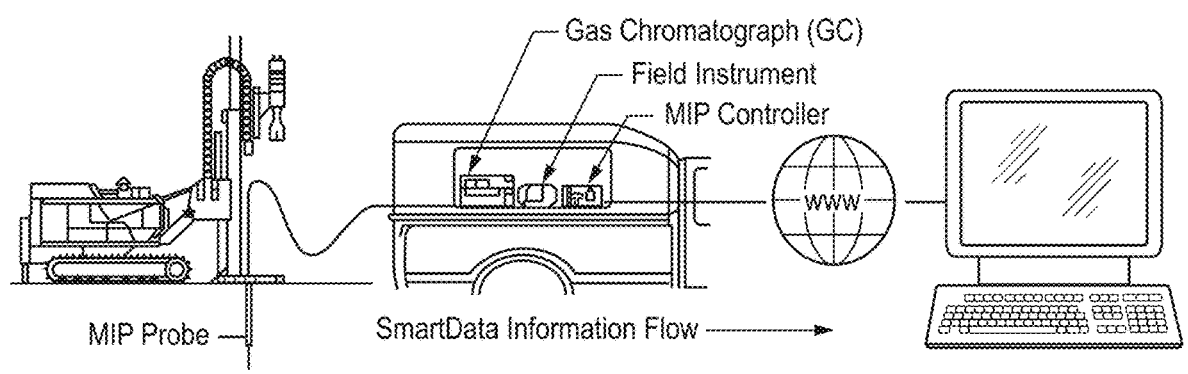
FIG. 2 is a schematic view of a typical configuration of a high density survey (including LIF).

As also discussed above, in accordance with another implementation, the oil sensing device 14 positioned in the well casing 10 can be a camera and a UV light source 13. As an example, FIG. 1 is a digital picture of a sand tank experiment using a combination of natural (visible) and UV light. The hydrocarbon was spiked with a fluorescent dye to enhance its fluorescence. However, other experiments show hydrocarbon can generate high quality images without the fluorescent dye (the sensitivity of UV photography with respect to LIF to low hydrocarbon saturations has not been tested, although it might be lower).

Figures 6A, 6B, 6C:
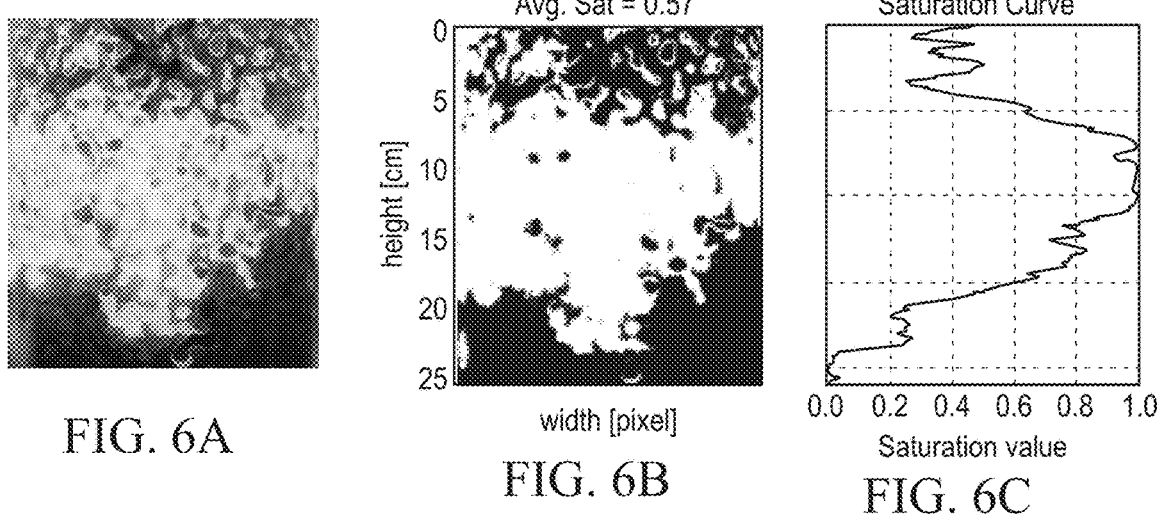
FIGS. 6A-6C depict the processing of the digital images to determine oil saturations in the soil, according to certain embodiments.

For the purposes of estimating LNAPL saturations in soils using fluorescence, the digital pictures can be evaluated qualitatively or by using digital imaging binarization techniques to quantitatively determine petroleum saturations. FIG. 6 shows the results of this technique.

In FIG. 6, the original digital image (left) is adjusted to binarize it (white pixels indicate fluorescence and NAPL presence, while black ones reflect the lack of it). The binary picture (center) is processed by averaging values across each elevation (values of 1 for white, 0 for black), determining average NAPL saturations at each elevation (right).

Although FIG. 6 was obtained from the outside of a sand tank experiment, use of a smaller camera with a short focal distance would enable taking such pictures from within a UV transparent well (as was the case for FIG. 11A). Off-the-shelf dental cameras have such capabilities (including deeming visible and UV lights separately), although these could be enhanced by providing supplemental light sources (either UV or visible).

As also mentioned above, according to one embodiment, the oil sensing device (not shown) positioned in the well casing 10 can be a probe coupled to a spectrometer. Fluorescence can be measured with standard spectrometers. As the location of the fluorescent compound is remote, a probe with fiber optics can be used to send excited light and signal. According to one embodiment, at least two types of probes can be used. One type is a probe in which the same light channel is used for the exciting incident light (UV) and the fluorescent signal. This might require timing of the signal measurement, as UV light can generate a noisy signal that interferes with the wavelength of the fluorescence. After excitation, fluorescence lasts in the order of 10-09 to 10-07 s (http://chemistry.rutgers.edu/grad/chem585/lecture2.html). Some applications of fluorescence collect the signal with a small delay after the excitation to reduce the noise due to the exciting light. The second type is a probe with multiple channels, some for excitation and some for fluorescence measurement, which can address the noise generated by the exciting light.

Figure 7:
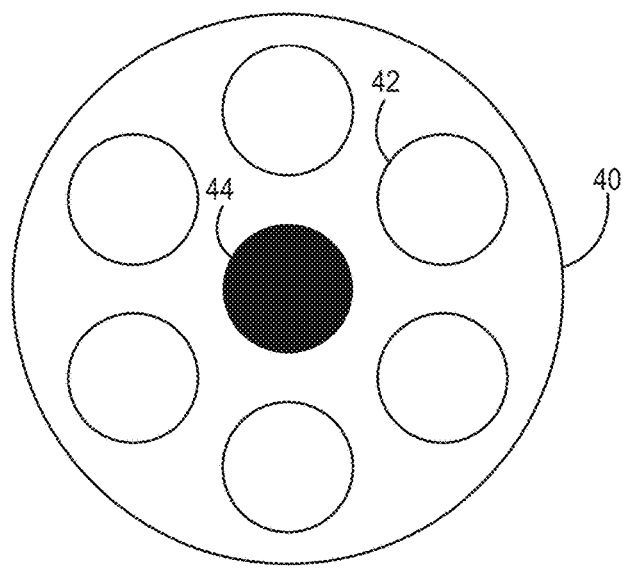
FIG. 7 is a cross-sectional view of an exemplary embodiment of a fiber optic probe, according to one implementation.

FIG. 7 shows a schematic diagram for one such probe 40. Fiber optics (FO) with exciting UV light are shown as open circles 42, fluorescence emission is conducted by the central FO 44 to the spectrometer for measurement.

Figure 8:
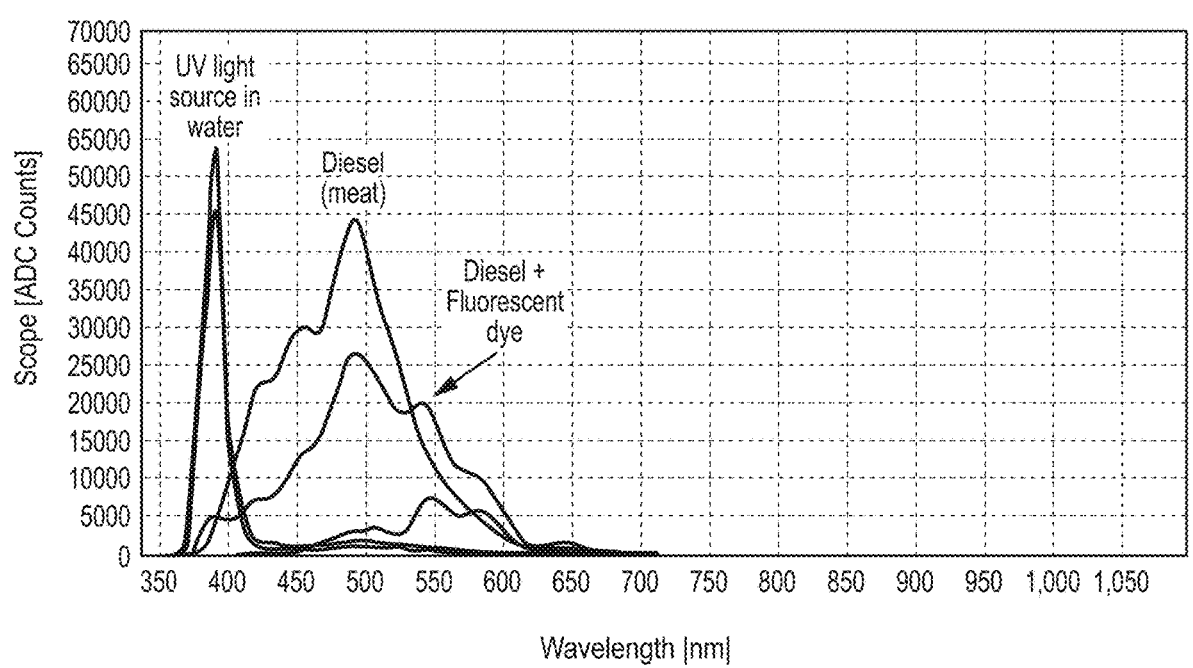
FIG. 8 shows the excitation signal as recorded by spectrometer (in combination with a fiber optic assembly as in FIG. 5).

FIG. 8 shows the signal obtained from diesel in soils using a spectrometer with a fiber optic array consisting of 6 incident channels (from a UV light source) surrounding a single signal channel feeding into a commercial spectrometer (Avantis).

FIG. 9 depicts an example showing a simulated oil spill in a sand tank 50. The sand tank includes porous media (sand), and water, to simulate groundwater. The example also included a UV-transparent well 12, a traditional half well 12 next to the sand tank glass, and a tube to feed water without wetting the sand. The sand tank was filled with sand as media 52, then water was added and allowed to equilibrate with the soil for about 10 hours to simulate groundwater. At that point, a contaminant 54 was added to simulate an oil spill.

This example used baby oil with added fluorescent dye as a model contaminant 54. Many contaminants (i.e., diesel or gasoline) fluoresce naturally. The (simulated) contaminant 54 shows up in these pics as bright yellow, and only does so when excited by UV light.

In this example, a simulated UV-transparent well 12, having a split casing 10, was inserted and set against the glass of the sand tank 50 for reference, to illustrate what type of information is available to practitioners using conventional monitoring wells.

In this example, a small camera was used in combination with UV and visible lights to observe the formation within the UV-transparent well 12, and compare it to the observations through the fish tank glass.

In FIG. 10, reference arrows show the saturated contaminant (LNAPL) 52 thickness in the example. Note that there is also a region of the soil (above the water table, a region known as the vadose zone, as discussed previously) where there is soil with low concentration of contaminant (called residual, when it will not drain further).

FIGS. 11A-11D depict further views of the example of FIGS. 9-10. That is, FIG. 11A depicts a close-up view of the interior of the well 12 made up of individual pictures pasted together. In FIG. 11B, the image of FIG. 11A has been binarized, that is, the image has been rendered as all white or all black, using specific criteria to determine what combination of the primary colors in each pixel of the original digital picture determine the presence or absence of fluorescence (i.e., contaminant). FIG. 11C depicts the saturation curve of the binarized image, showing the contaminant 54 saturation (the percent of pixels where there is fluorescence) at each elevation.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

The invention claimed is:

1. A method for measuring non-aqueous phase liquids ("NAPLs") comprising:
    emplacing a sealed well casing into a media forming a dry well;
    inserting a sensing device and UV light source into the sealed well casing;
    exciting fluorescence of NAPL with the UV light source;
    capturing an image of the fluorescence; and
    processing the image to quantitatively determine an amount of NAPL in the media.

2. The method of claim 1, wherein no external materials are added around the sealed well casing while emplacing the well.

3. The method of claim 1, further comprising freezing the media.

4. The method of claim 1, wherein the sensing device comprises a laser-induced fluorescence probe.

5. The method of claim 1, further comprising identifying characteristics of the NAPLs via measuring red, green and blue emissions of the fluorescence.

6. The method of claim 1, wherein the sensing device comprises a camera and further comprising determining particle size of the media.

7. The method of claim 1, wherein the processing comprises digital imaging binarization.

8. A system for detecting NAPL and petroleum comprising:
    (a) a UV transparent well casing;
    (b) an oil sensing device comprising a camera;
    (c) a display; and
    (d) a processor constructed and arranged to process signals from the sensing device to quantify the amount of NAPL in the media,
    wherein the display is constructed and arranged for visualization of soil fluorescence and soil features, and wherein the processor is further constructed and arranged to determine average NAPL saturations at various elevations.

9. The system of claim 8, wherein the UV transparent well casing forms a dry well.

10. The system of claim 9, wherein the oil sensing device further comprises a UV light source.

11. The system of claim 10, wherein the soil features visualized include at least one of grain size and color.

12. The system of claim 8, wherein the oil sensing device further comprises a spectrometer.

13. The system of claim 12, wherein the oil sensing device further comprising a fiber optic probe.

14. The system of claim 8, wherein the UV transparent well comprises at least one of clear PVC, polymethyl pentene (PMP), UV transparent acrylic, and glass.

15. A kit for detecting non-aqueous phase liquid (NAPL) in a media comprising:
   (a) a UV light source;
   (b) a sensing device;
   (c) a UV transparent well casing; and
   (d) a processor constructed and arranged to process signals from the sensing device to quantify the amount of NAPL in the media,
   wherein the processor is further constructed and arranged to determine average NAPL saturations at various elevations.

16. The device of claim 15, wherein the sensing device further comprises a fiber optic device in communication with a spectrometer.

17. The device of claim 15, wherein the sensing device further comprises a digital camera.

18. The device of claim 15, wherein the sensing device further comprises a light induced fluorescence probe.

19. The device of claim 15, wherein the processor is constructed and arranged to quantitatively determine NAPL saturations via digital imaging binarization.

\* \* \* \* \*